United States Patent [19]

Maryanoff et al.

[11] 4,454,319
[45] Jun. 12, 1984

[54] PYRIMIDO[6,1-A]ISOQUINOLINE-4-ONE DERIVATIVES

[75] Inventors: Bruce E. Maryanoff, New Hope; Albert J. Molinari, Philadelphia, both of Pa.

[73] Assignee: McNeilab, Inc., Fort Washington, Pa.

[21] Appl. No.: 383,422

[22] Filed: Jun. 1, 1982

[51] Int. Cl.³ .................. C07D 471/04; A61K 31/505
[52] U.S. Cl. ...................................... 544/252; 424/251
[58] Field of Search ........................ 544/252; 424/251

[56] References Cited

U.S. PATENT DOCUMENTS 3,021,331  2/1962  Lombardino et al. .............. 544/252
3,337,580  8/1967  Lunsford et al. ................ 544/132 X

OTHER PUBLICATIONS

Maryanoff et al., J. Med. Chem., vol. 24(1), pp. 79-88, (01/81).
Maryanoff et al., Tetrahedron Letters, No. 28, pp. 2829-2832, (1982).
Nair et al., Chemical Abstracts, vol. 71, 101682v, (1969).
Kaneko et al., Chemical Abstracts, vol. 75, 36106b, (1971).
Lal et al., Chemical Abstracts, vol. 93, 220770m, (1980).

Primary Examiner—Mary C. Lee
Assistant Examiner—Diana G. Rivers

[57] ABSTRACT

Pyrimido[6,1-a]isoquinoline-4-one derivatives of the formula:

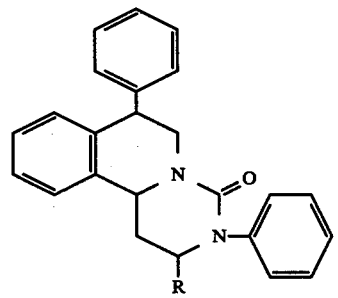

I wherein R is $C_1$–$C_6$ lower alkyl or 2-haloethyl (halo=Cl, Br or I) having antihypertensive activity.

2 Claims, No Drawings

PYRIMIDO[6,1-A]ISOQUINOLINE-4-ONE DERIVATIVES

This invention relates to novel compounds, which embody the 1H-pyrimido[6,1-a]isoquinoline ring system and to novel processes for the preparation of such compounds. More particularly, the invention is concerned with novel compounds represented by the following formula (I),

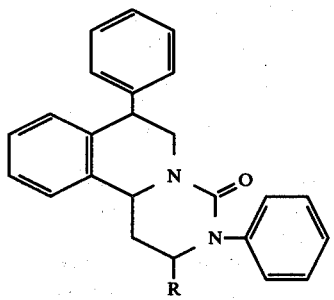

I wherein R is $C_2-C_6$ lower alkyl or 2-haloethyl (halo=Cl, Br or I).

The formula I compounds exhibit antihypertensive activity. The most preferred group of compounds is exemplified by formula II.

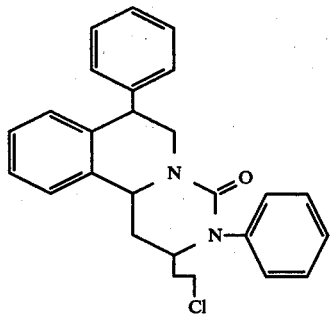

Compounds of formula II may be prepared by reacting anilines of structure III with phosgene, followed by treatment with an amine. A novel rearrangement of the intermediate carbamyl chloride IV thereby occurs to afford formula II compounds of this invention. Certain amines will work in this reaction, such as strongly basic tertiary amines (e.g., triethylamine, or ethyl diisopropylamine) and $CF_3CH_2NH_2$, whereas weakly basic tertiary amines (e.g., dimethylaniline) or pyridine are not especially suitable.

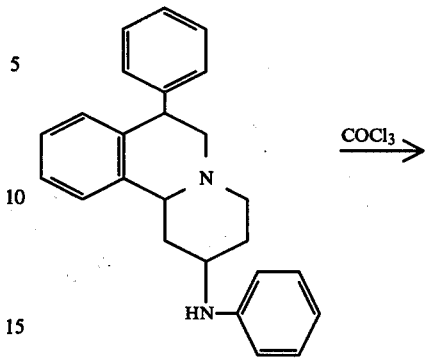

III

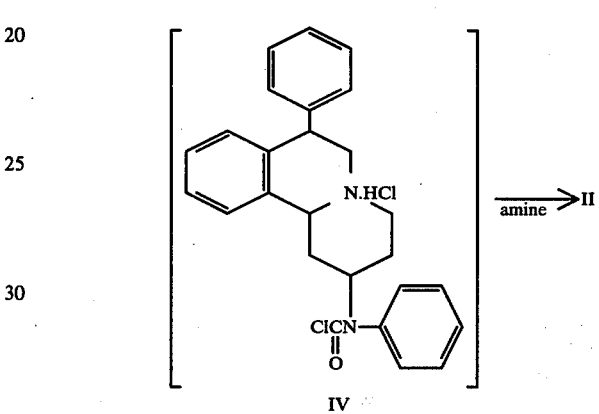

IV

The bromo analog of II is prepared by using $COBr_2$ in place of $COCl_2$, and the iodo analog of II is prepared by reaction of II with an alkali metal iodide such as sodium or potassium iodide in a polar solvent such as acetone. The aniline starting materials are prepared according to described procedures [B. Maryanoff, et al., J. Med. Chem., 24,79 (1981)].

The loweralkyl derivatives of I may be prepared by chemical modification of haloethyl derivatives, as illustrated in an exemplary manner by the equations presented hereinafter.

Modification of haloethyl derivatives to give alkyl derivatives

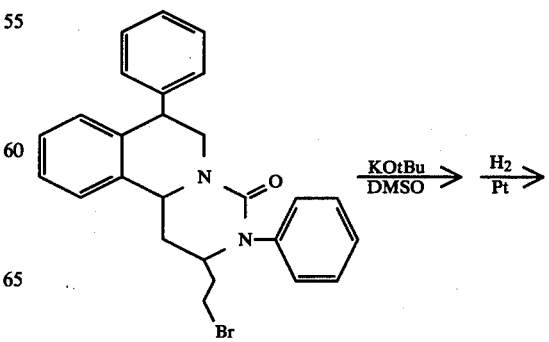

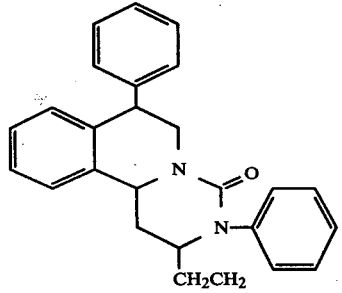

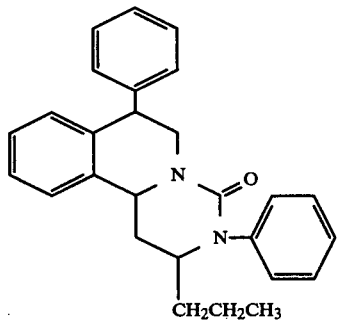

As can be seen, what the above reaction scheme illustrates is how, using well known techniques, the bromoethyl side-chain can be extended by use of a lithium dialkylcuprate reagent, such as LiCu(CH$_3$)$_2$ (q.v. G. H. Posner, Org. Reactions, 22, 253 (1975)). Also, that the bromoethyl side-chain can be converted to a vinyl group with a strong base such as potassium t-butoxide (KOtBu) in dimethyl sulfoxide (DMSO) solvent (q.v. N. F. Wood and F. C. Chang J. Org. Chem. 30, 2054 (1965) and, such a vinyl compound can be converted to an ethyl group by catalytic hydrogenation (e.g., H$_2$ with platinum (q.v. R. L. Augustine, "Catalytic Hydrogenation", Marcel Dekker, Inc. (1965)).

The formula II compounds of this invention are endowed with useful biological activity in the cardiovascular system. In particular, the claimed compounds lower blood pressure in warm-blooded animals, and thus are useful as antihypertensive agents. The utility of the compounds is based on a standard test for antihypertensive agents in rats, which possess normally elevated blood pressure. This test is described hereinafter.

Rodent Antihypertensive Screen

This test evaluates compounds for effects on arterial pressure and heart rate. In this test, the arterial pressure of adult spontaneously hypertensive rats [SHR] (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

Compound II reduced MAP by 34 mm Hg on i.p. administration of 30 mg/kg without any increase in heart rate.

The following examples illustrate the preparation of the compounds of the present invention, but are not to be construed as limiting.

EXAMPLE I 1,3,4,6,7,11b-Hexahydro-2-(2-chloroethyl)-3,7-diphenyl-1H-pyrimido[6,1-a]isoquinolin-4-one 3.39 g (9.56 mmol) of 1,3,4,6,7,11b-hexahydro-N,7-diphenyl-2H-benzo[a]quinolizin-2-amine is treated with excess phosgene at −20° C. in dry methylene chloride then allowed to stir at room temperature for 0.5 hrs. The solvent is removed in vacuo to give an amorphous solid intermediate. The intermediate is redissolved in methylene chloride, treated with excess 2,2,2-trifluorethanamine at room temperature and allowed to stir overnight. The reaction mixture is filtered and the solvent removed in vacuo. The resulting oil is redissolved in methylene chloride, washed with 0.1N HCl, followed by water, and the organic phase is dried over potassium carbonate. The solvent is removed in vacuo and the oil crystallized from ethyl acetate-hexane. Recrystallization from ether affords II as white solid, 165°–167° C.

EXAMPLE II

By following the procedure of Example I, but replacing the phosgene (COCl$_2$) with equivalent amounts of COBr$_2$, there may be obtained 1,3,4,6,7,11b-hexahydro-2-(2-bromoethyl)-3,7-diphenyl-1H-pyrimido[6,1-a]isoquinolin-4-one.

What is claimed is:

1. A compound of the formula

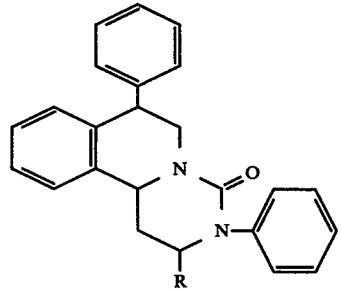

wherein R is ethyl, n-propyl or 2-haloethyl, wherein the halo=Cl, Br, or I.

2. The compound of claim 1 which is 1,3,4,6,7,11b-hexahydro-2-(2-chloroethyl)-3,7-diphenyl-1H-pyrimido[6,1-a]-isoquinolin-4-one.

* * * * *